United States Patent [19]

Liprie

[11] Patent Number: 5,618,266
[45] Date of Patent: Apr. 8, 1997

[54] CATHETER FOR MANEUVERING RADIOACTIVE SOURCE WIRE TO SITE OF TREATMENT

[76] Inventor: Samuel F. Liprie, 424 W. McNeese St., Lake Charles, La. 70605

[21] Appl. No.: 316,500

[22] Filed: Sep. 30, 1994

Related U.S. Application Data

[63] Continuation-in-part of Ser. No. 220,681, Mar. 31, 1994, Pat. No. 5,556,389.

[51] Int. Cl.⁶ ........................................ A61N 1/30
[52] U.S. Cl. .............. 604/21; 604/96; 604/264; 600/3; 606/194
[58] Field of Search .................. 604/96, 19, 20, 604/21, 264, 265, 246–249; 606/191, 192, 194; 128/657, 772; 600/1–3, 7

[56] References Cited

U.S. PATENT DOCUMENTS

| | | | |
|---|---|---|---|
| 4,932,959 | 6/1990 | Horzewski | 604/96 |
| 5,024,658 | 6/1991 | Kozlov | 604/101 |
| 5,106,360 | 4/1992 | Ishiwara | 600/3 |
| 5,158,553 | 10/1992 | Berry | 604/169 |
| 5,160,321 | 11/1992 | Sahota | 604/96 |
| 5,174,302 | 12/1992 | Palmer . | |
| 5,199,939 | 4/1993 | Dake et al. . | |
| 5,209,730 | 5/1993 | Sullivan . | |
| 5,213,561 | 5/1993 | Weinstein et al. . | |
| 5,256,150 | 10/1993 | Quiachon | 604/171 |
| 5,295,959 | 3/1994 | Gurbel | 604/96 |
| 5,308,356 | 5/1994 | Blackshear | 606/194 |
| 5,318,587 | 6/1994 | Davey | 604/96 |
| 5,324,259 | 6/1994 | Taylor | 604/96 |
| 5,326,343 | 7/1994 | Rudie | 607/101 |
| 5,346,505 | 9/1994 | Leopold | 604/96 |
| 5,360,403 | 11/1994 | Mische | 604/101 |
| 5,368,567 | 11/1994 | Lee | 604/96 |
| 5,370,676 | 12/1994 | Sozanki | 607/101 |
| 5,378,237 | 1/1995 | Boussignae | 604/96 |
| 5,389,087 | 2/1995 | Miraki | 604/247 |
| 5,395,333 | 3/1995 | Brill | 604/101 |
| 5,397,305 | 3/1995 | Kawula | 604/96 |
| 5,431,648 | 7/1995 | Leu | 607/101 |
| 5,441,485 | 8/1995 | Peters | 604/101 |

*Primary Examiner*—Randall L. Green
*Assistant Examiner*—Chalin Smith
*Attorney, Agent, or Firm*—Hoffman, Wasson & Gitler, P.C.

[57] ABSTRACT

An apparatus for treating an occlusion or constriction, such as a stenosis in a blood vessel or other conduit in the body, as well as an apparatus for treating bodily diseases (e.g. a tumor or cancerous area) occurring around a conduit or duct in the body. The apparatus includes a catheter which is correctly positioned within a conduit of the body utilizing a guide wire. The guide wire would pass through the entire length of the catheter, or a portion of the length of the catheter, and would exit the catheter through a constriction plug affixed to the end of the catheter. A radioactive treatment source wire is then introduced into the catheter and is maneuvered to the site of treatment. The constriction plug is provided with an internal diameter which is less than the diameter of the radioactive source wire, but greater than the diameter of the guide wire. This construction would prevent the radioactive source wire from remaining in the body after the catheter has been removed.

22 Claims, 10 Drawing Sheets

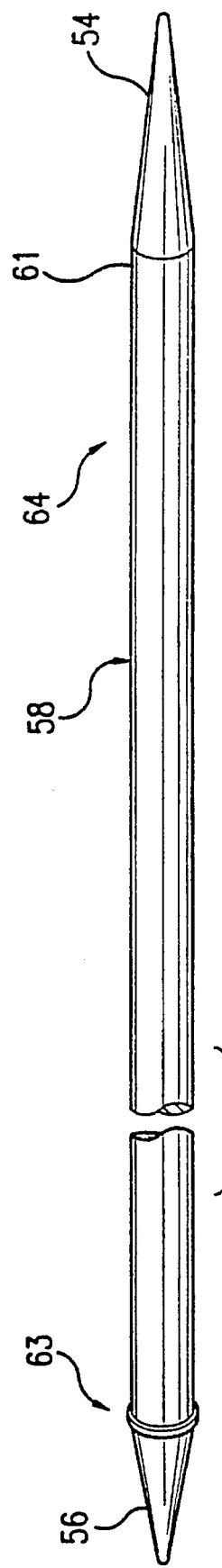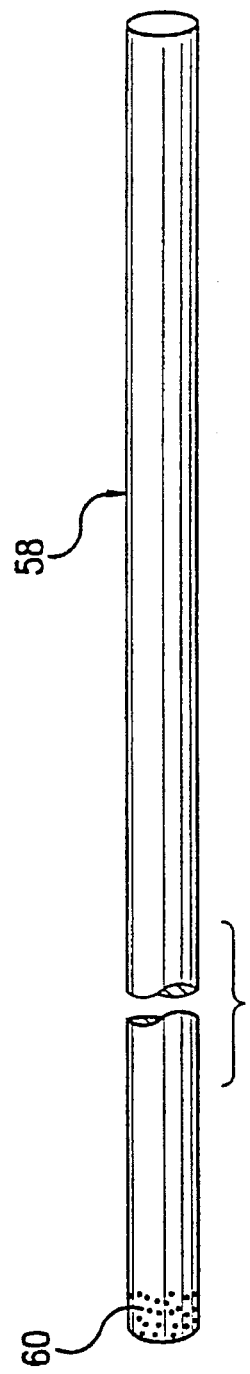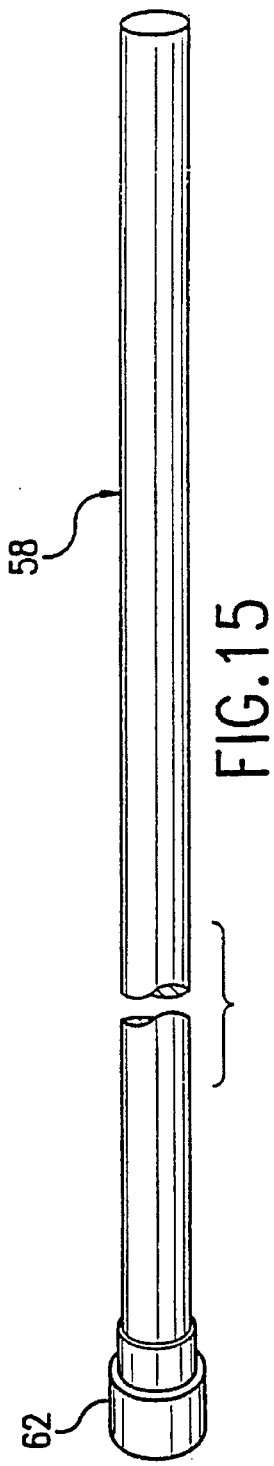

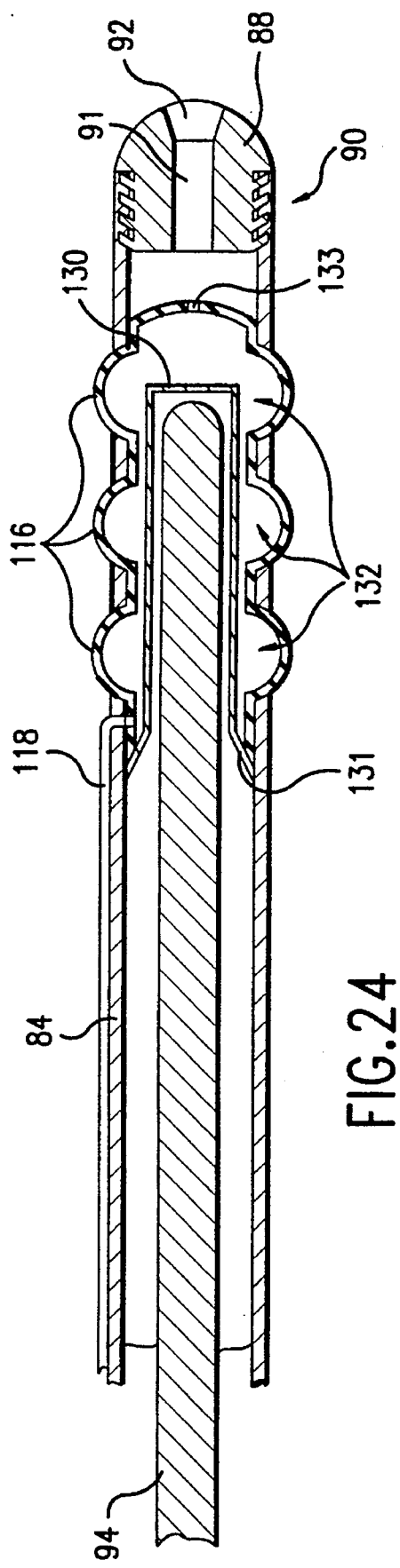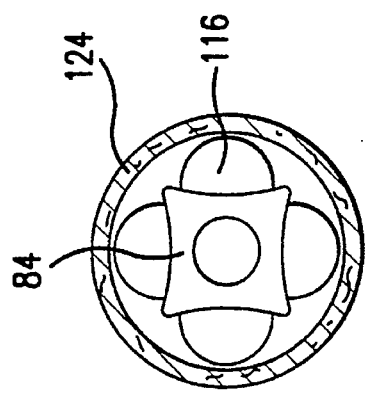
FIG. 24
FIG. 25

CATHETER FOR MANEUVERING RADIOACTIVE SOURCE WIRE TO SITE OF TREATMENT

RELATED APPLICATIONS

The present application is a continuation-in-part application of U.S. patent application Ser. No. 08/220,681, filed Mar. 31, 1994, now U.S. Pat. No. 5,556,389.

BACKGROUND OF THE INVENTION

1. Field of the Invention

The present invention relates to the field of treating a stenosis which would occur in various blood vessels and other bodily conduits as well as to the field of angioplasty. Additionally, the present invention is directed to the field of treating cancer which would occur in various body conduits or ducts, as well as to the field of brachytherapy.

2. Description of the Prior Art

Various techniques have been developed to treat many different conduits in the body when these conduits have become reduced in size due to the existence of a stenosis or have been completely occluded. These techniques include introducing a deflated balloon catheter to the site of the stenosis or occlusion, inflating the balloon one or more times to eliminate the size of the stenosis, deflating the balloon and then removing the balloon catheter from the treatment site.

With respect to the vascular pathways, angioplasty is used to open an artery or blood vessel in the region where the stenosis or the occlusion has occurred. A typical angioplasty procedure consists of making a small incision through the body and into a blood vessel and then maneuvering a guide wire through the vascular system to a point beyond the stenosis or occlusion. A hollow catheter with a deflatable balloon near its distal end is threaded over the guide wire and advanced to the point of stenosis or occlusion. The balloon is then inflated and deflated several times to widen the constricted area, and is then withdrawn from the body.

Unfortunately, although the angioplasty procedure does markedly reduce the area of stenosis or occlusion, many patients exhibit a reoccurrence of the stenosis within a few months of the original procedure.

Although the original stenosis occurs by means of the build up of plaque over a relatively long period of time, experimentation has lead many to believe that the reoccurrence of the stenosis after the original angioplasty procedure is unrelated to the cause of the original stenosis. It is believed that the inflation of the balloon catheter used in the angioplasty procedure or the placement of a stent in the area of the stenosis causes irritation to the blood vessel. This irritation produces a mechanism of action called hyperplasia, inducing the inner layer of the blood vessel cells to rapidly reproduce, thereby causing restenosis. It has been proposed that if the blood vessel is irradiated at the point of the stenosis with a radioactive dose, the mechanism that causes hyperplasia would be destroyed without harming the blood vessel itself.

During this procedure, it is important to precisely control the amount of radiation which is directed to the blood vessel wall, since too much radiation could actually induce hyperplasia as well as destroying a portion of the blood vessel, making it possible for an aneurism or rupture to occur. U.S. Pat. No. 5,213,561 issued to Weinstein et al and U.S. Pat. No. 5,199,939 issued to Dake et al, as well as PCT Application PCT/US92/07447 to Shefer et al, describe various methods and apparatus for introducing radiation to the site of a stenosis to endeavor to prevent restenosis.

The Weinstein et al patent describes a method and apparatus for preventing restenosis after angioplasty. A balloon catheter transported by a conventional guide wire is delivered to the location of the stenosis. Particles or crystals of radioactive material are embedded or mounted on a tube provided inside the balloon catheter. A retractable radiation shielding sleeve is slidable along the tube to cover the source of radioactive material. Upon completion of the angioplasty, the shielding sleeve is retracted and the area of the stenosis is irradiated. Although this apparatus does introduce radiation to the point of the stenosis, the retractable shielding surrounding the source of radioactive material makes this catheter bulky and unwieldy to use. In this regard, it is very doubtful that a catheter system this bulky would fit into the smaller branches or vessels of the heart. It is also doubtful that a catheter this bulky and stiff could be maneuvered through the tighter bends and turns in many of the vessels.

An additional embodiment of the Weinstein et al patent illustrates a stent which is made of or coated with a radioactive material such as iridium 192. Since the radioactive material is provided on the outer surface of the stent, it is very difficult to precisely administer the proper dosage of radiation to prevent hyperplasia without administering a level of radiation which would actually induce hyperplasia or other deleterious effects to the blood vessel.

The PCT application illustrates a method and apparatus for restenosis treatment by applying a radioactive dose to the stenosed region after reduction of the region by angioplasty or other means. As shown in FIG. 4, an angioplasty balloon is expanded in the vicinity of a lesion site and radioactive elements provided on the exterior surface of the balloon are forced into contact with the region. Therefore, similar to the Weinstein et al patent, the presence of the radioactive material on the exterior of the catheter would make it very difficult to apply the precise amount of radiation to the region of interest. Additionally, both the PCT application as well as the patent to Weinstein describe balloon catheters which do not allow the blood within the vessel to flow during inflation of the balloon.

The patent to Dake et al shows a radioactive catheter for preventing restenosis after angioplasty. However, this patent merely indicates that an elongated flexible catheter is transported to the area of the original stenosis after a balloon catheter has been withdrawn, thereby lengthening the time to administer the entire procedure.

SUMMARY OF THE INVENTION

These and other deficiencies of the prior art are addressed by the present invention which is directed to a method and apparatus for treating the location of a stenosis in a blood vessel or other hollow conduit in the body by inflating and deflating a balloon catheter one or more times. A source of radiation is then advanced through the catheter to the site of the stenosis, centered within the blood vessel, and the site is then treated for a period of time with radiation. Once the treatment is completed, both the radiation source and the balloon catheter are withdrawn.

According to the teachings of the present invention, a radiopaque guide wire is inserted into the body through a small incision and is then introduced into a blood vessel or similar conduit. Once in place, a catheter having a ribbed balloon attached near the distal end thereof is threaded over the guide wire and is also advanced to the location of treatment. The interior of the catheter is provided with an elastic membrane, one-way valve or other similar device for sealing the distal end of the catheter, but allowing the guide wire to pass therethrough. The guide wire is then removed and the ribbed balloon is inflated one or more times to reduce the size of the stenosis, while allowing blood to flow around the site of the stenosis to greatly decrease the patient's risk of a myocardial infarction or heart attack. A radioactive source is advanced into position through the balloon catheter to the site of the original stenosis. With the balloon inflated, the balloon catheter and the radioactive source are correctly centered within the blood vessel to administer a precise dose to the original area of the stenosis. After a period of time in which the original site of the stenosis is irradiated from the radioactive source, both the radioactive source and the balloon catheter are then removed from the blood vessel and the body of the patient.

Contrast dye, helpful in locating the position of the catheter within a body vessel is injected therein by a conduit provided on the exterior surface of the catheter or through the guide wire itself, after the core of the guide wire has been removed.

The distal end of the catheter could alternatively be sealed utilizing a constriction plug affixed to the end of the catheter. The constriction plug can be the same diameter of the catheter itself and is rounded to prevent trauma as the catheter maneuvers through the body. The constriction plug is provided with an internal passageway having a diameter which is less than the diameter of the radioactive source wire, but greater than the diameter of the guide wire. This construction would allow the guide wire to pass through the constriction plug, but would prevent the radioactive source wire from exiting the distal end of the catheter, thereby assuring that the radioactive guide wire would not remain behind in the body when the catheter is withdrawn.

BRIEF DESCRIPTION OF THE DRAWINGS

The above and other objects, features and advantages of the present invention will become apparent from the following description and the appended claims, taken in conjunction with the accompanying drawings, in which:

FIG. 13 is a side view of a removable core guide wire inserted into the body;

FIG. 14 is a side view of the guide wire shown in FIG. 13 after the core has been removed;

FIG. 15 is a side view of the guide wire shown in FIG. 14 after a Luer-Lock has been attached thereto;

FIG. 24 is a longitudinal sectional view of another embodiment of FIG. 21 using the internal, inflatable sealing device as a centering device also;

FIG. 25 is an end view of FIG. 24 with the catheter centered inside a bodily conduit;

DETAILED DESCRIPTION OF THE PREFERRED EMBODIMENTS

Although the present invention can be used to treat blockages in many body conduits, for ease of explanation, the present invention will be discussed with respect to a stenosis provided in a blood vessel.

Figure 1:
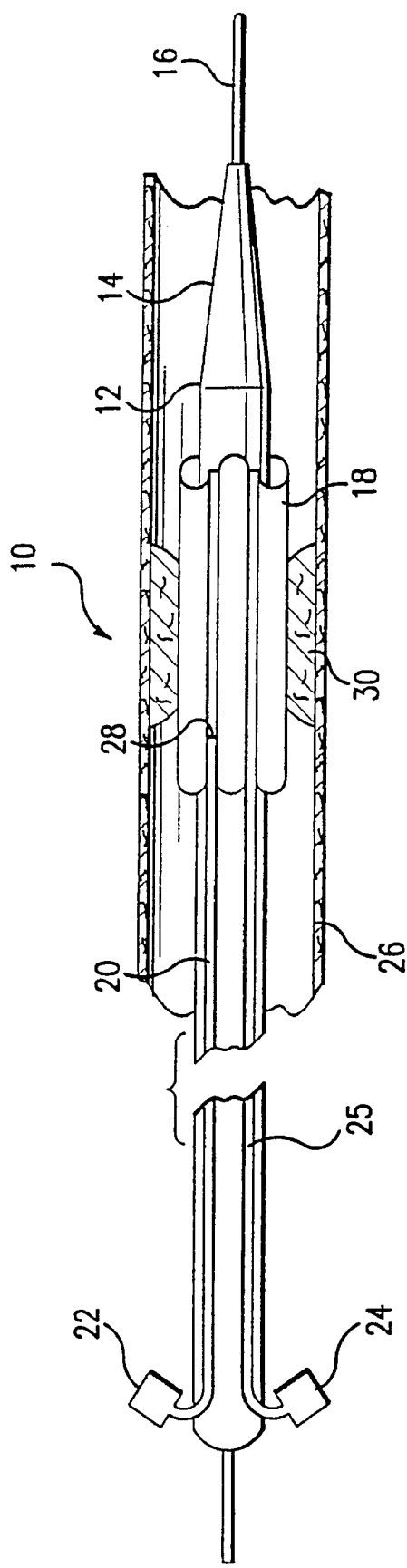
FIG. 1 is a side view of a ribbed balloon catheter according to the present invention.
Figure 2:
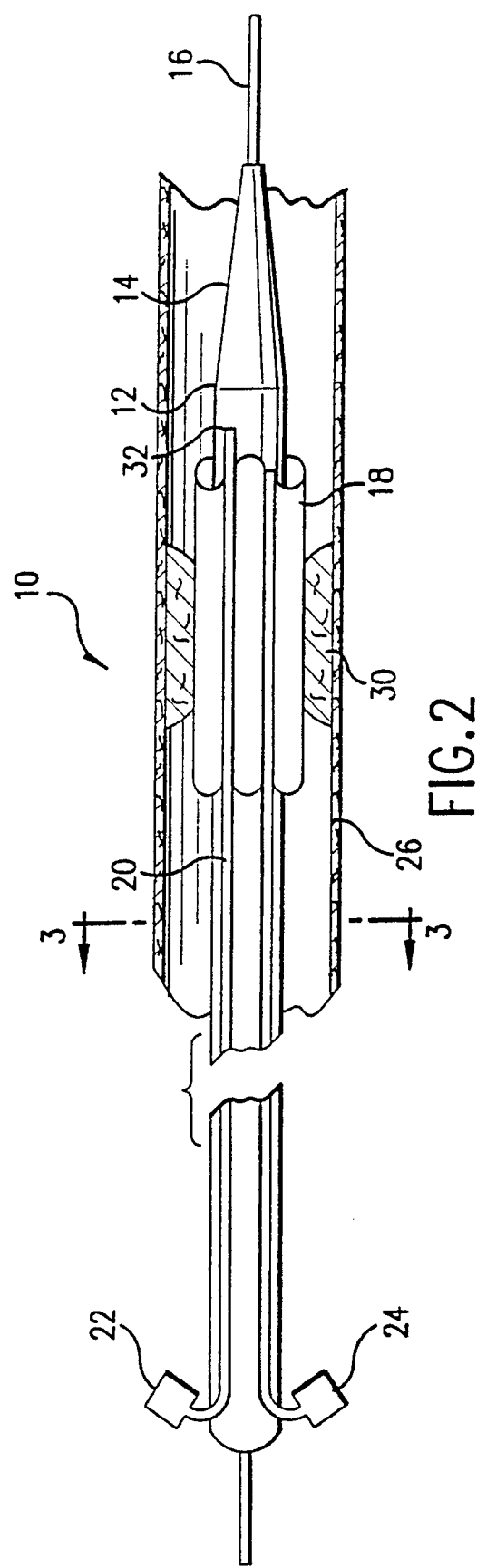
FIG. 2 is a side view of a second embodiment of the ribbed balloon catheter according to the present invention.
Figure 3:
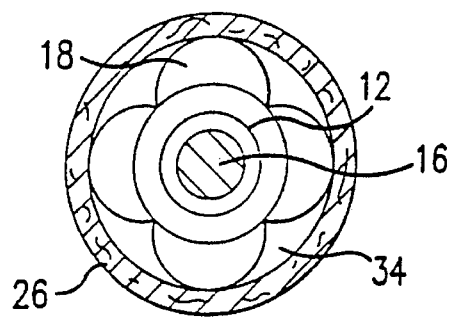
FIG. 3 is a transverse cross-sectional view of the ribbed balloon catheter of the present invention taken along lines 3—3 of FIG. 2.

FIGS. 1, 2 and 3 illustrate the catheter 10 of the present invention after it has been inserted into the body and moved to the site of a stenosis 30 in a blood vessel 26. The catheter itself consists of a hollow, generally cylindrical member 12 which is constructed from a fairly flexible material such as polyethylene glycol so that it can be easily maneuvered within the body and travel over a guide wire 16 which was initially maneuvered in the blood vessel to a position beyond the actual site of the stenosis. The interior of the catheter can be made of or coated with a friction reducing material, such as TEFLON (PTFE) to aid in the passing of the guide wire and the radioactive sources to the treatment site. The catheter itself is slightly tapered at its distal end 14 to facilitate movement through blood vessels or similar conduits or ducts. Both the guide wire 16 and the catheter 12 should be of sufficient length to travel to the site of occlusion or constriction in various conduits and certainly should be long enough to reach the heart. A ribbed balloon 18 surrounds a portion of the outer surface of the catheter 12 and contains a number of ribbed pleats. When these pleats are inflated by a syringe 24 injecting air into a conduit 25 extending along the exterior surface of the catheter 12 to the balloon 18, the size of the stenosis would be reduced as well as allowing the catheter to be properly centered when a radioactive source is introduced to the original site of the stenosis.

A second syringe 22 is also attached to the catheter 12 for injecting contrast dye into the blood vessel to aid in the proper location of the catheter. This contrast dye would travel through a conduit 20 also provided on the exterior surface of the catheter to a site 28 near the proximal end of the balloon 18 (see FIG. 1) or could extend to a point 32 beyond the distal end of the balloon 18 (see FIG. 2).

Alternatively, contrast dye can be introduced to the site of the stenosis by injecting the contrast dye directly into the interior of the catheter 12. This is accomplished utilizing a guide wire provided with a removable core, the operation of which will be subsequently explained.

Since the ribbed balloon 18 would inflate in a symmetrical pattern, blood would be allowed to profuse at various locations 34 during both the angioplasty procedure as well as the radiation treatment. This flow of blood would greatly decrease the incidence of a myocardial infarction or a heart attack and would allow the angioplasty procedure as well as the radiation treatment to be performed as long as needed without completely blocking the flow of blood through the vessel.

Since the catheter of the present invention would act as a conduit to allow a radiation source to be introduced to the site of the original stenosis, it is important that the catheter should be sealed at a point proximate to its distal end, while allowing a guide wire to exit the distal end of the catheter 12. Consequently, the present invention utilizes an elastic membrane 40 shown in FIGS. 4, and 6–9 to perform this function. This membrane can be constructed of any biocompatible material 44 that will expand large enough to allow the guide wire 16 to pass therethrough and then contract to form a closed seal when the guide wire is removed.

Figure 9:
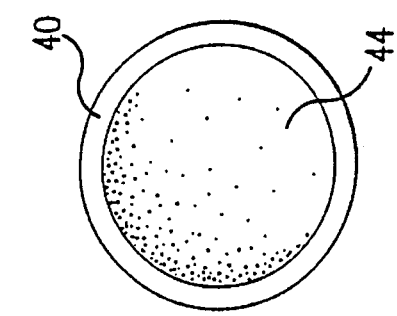
FIGS. 6–9 are end views of the elastic membrane shown in FIG. 4 with or without the guide wire inserted therethrough.
Figure 8:
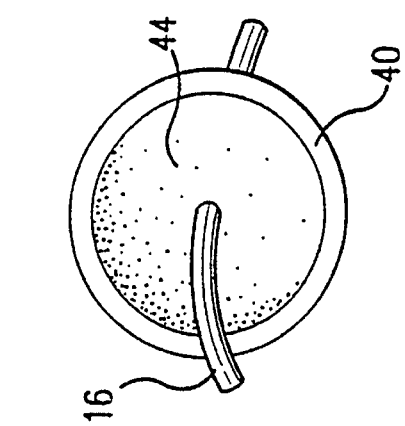
Figure 7:
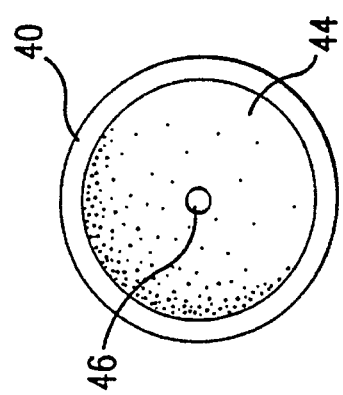
Figure 6:
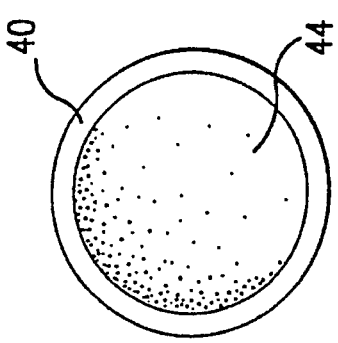
Figure 12:
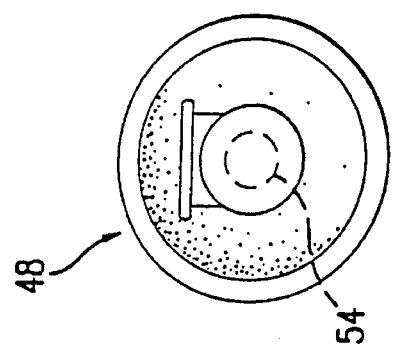
FIG. 12 is a front view of the one-way valve showing the smaller opening behind the flap.
Figure 11:
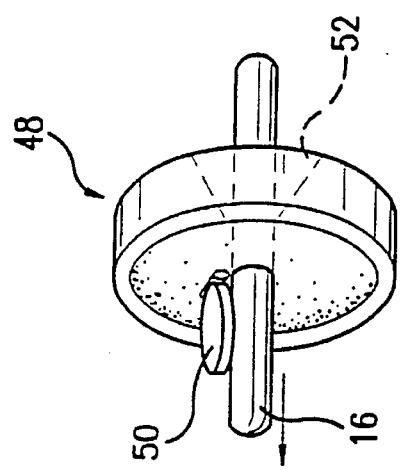
FIG. 11 is a side view of the one-way valve with the guide wire passing therethrough.
Figure 10:
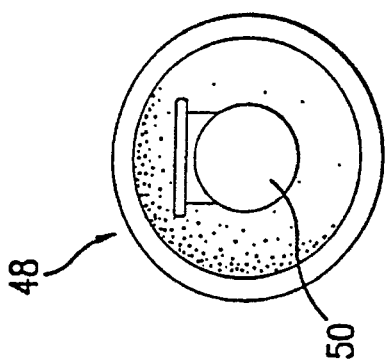
FIG. 10 is a front view of the one-way valve shown in FIG. 5.

FIG. 6 illustrates the elastic membrane which is completely sealed prior to the guide wire passing through this membrane. FIG. 7 illustrates the membrane with a small hole 46 forming in the middle thereof which would allow the guide wire to pass therethrough as shown in FIG. 8. FIG. 9 illustrates the elastic membrane 40 immediately after the guide wire 16 has been removed.

Figure 4:
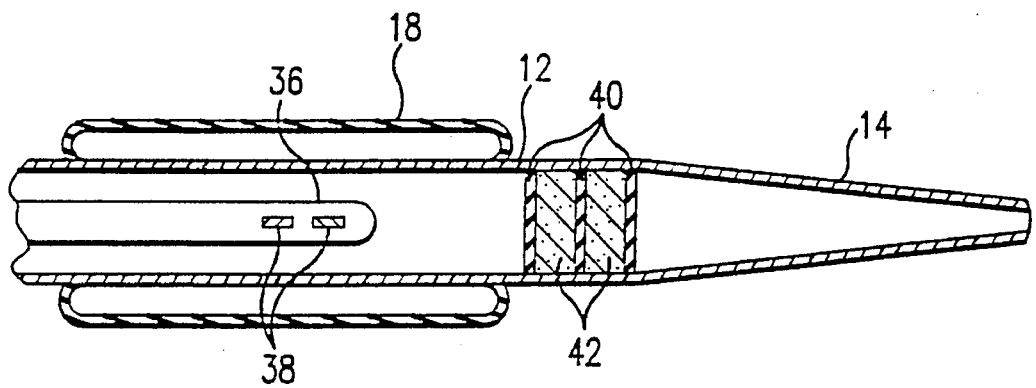
FIG. 4 is a longitudinal sectional view of the ribbed balloon catheter of the present invention showing the radioactive source within the balloon catheter.

As shown in FIG. 4, more than one elastic membrane 40 can be utilized to insure that the catheter is sealed after the guide wire 16 is removed. Regardless of whether a single membrane or a plurality of membranes are used, the membrane is placed in the interior of the catheter 12 at a location beyond the ribbed balloon 18, in such a manner as to effectively seal the catheter from the blood vessel. Filters 42 can be provided between each of these membranes for wiping the guide wire as it travels through the balloon catheter 12. Because the guide wire 16 extends into the blood vessel, and is then removed from the catheter 12 after the catheter has been maneuvered to the correct location, it is important that blood or other liquids not be introduced into the sealed portion of the catheter since this would inhibit the proper placement of the radioactive source. The filtered material 42 can be constructed from any biocompatible material that freely allows the guide wire 16 to pass therethrough as well as wiping the guide wire as it is withdrawn from the catheter 12. Cotton or angel foam have been found to be particularly efficacious for this purpose.

An alternative embodiment in which a one-way valve 48 is used with, or in place of the elastic membrane 40 is shown in FIGS. 5, 10, 11 and 12. The one-way valve 48 is placed in the interior of the catheter beyond the ribbed balloon 18.

Figure 5:
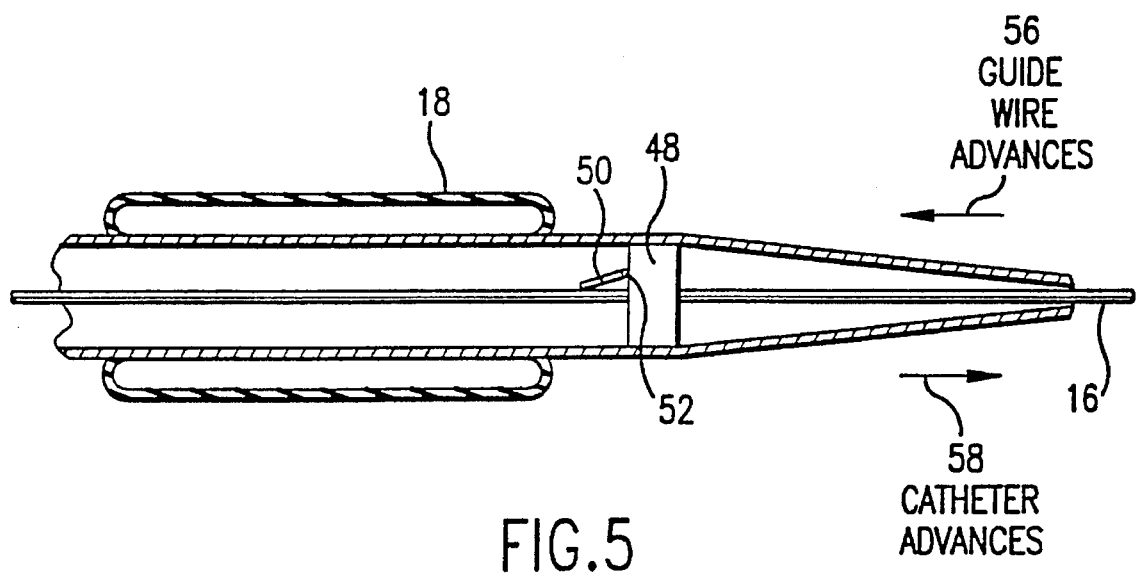
FIG. 5 is a longitudinal sectional view of the present invention showing the guide wire and the one-way valve.

The one-way valve is provided with a relatively large flap 50 which is considerably larger than the hole 54 which it covers. A tension hinge 52 insures that the flap remains in the closed position during the absence of the guide wire 16. In use, as shown in FIG. 5, the guide wire 16 advances in the direction shown by arrow 56 and the catheter advances in the direction shown by arrow 58. In this instance, as the guide wire passes through the relatively small hole 54, it pushes against the flap, causing the flap to rise and allow passage of the guide wire therethrough. As illustrated in FIG. 5, since the hole 54 is much smaller than the size of the flap 50, the flap can only move in the clockwise direction and not in the counterclockwise direction. A "funnel-shaped" entry port 52 assists in allowing the guide wire 16 to pass through the hole 54. If the one-way valve is used in conjunction with at least one of the elastic membranes 40 shown in FIG. 4, filter material 42 can be provided between these two sealing members.

FIGS. 13–15 demonstrate a removable core guide wire 64 which can be used instead of the guide wire 16 illustrated in FIGS. 1 and 2. The guide wire 64 is provided with a flexible outer housing 58 which can be constructed from such a material as nitinol. The removable core guide is provided within the outer housing 58 and includes a soft, flexible, rounded tapered end leader 54 extending beyond one end 61 of the outer housing 58. A slightly oversized cap 56 is provided over the second end 63 of the outer housing 58 to allow the removable core to be removed from the outer housing with the guide wire has been properly positioned within the blood vessel. Once the core is removed, the guide wire would only include the hollow outer housing 58 as well as a series of external threads 60 on the end of the guide wire extending out of the patient's body. This threading would allow a Luer-Lock 62 or similar device to be screwed onto the outer housing 58 so that a syringe can inject contrast dye into the catheter. The removable core can be constructed from Teflon, nitinol or any springy, soft biocompatible material. If the removable guide wire as illustrated in FIGS. 13–15 is employed, the conduit 20 shown in FIGS. 1 and 2 used to deliver contrast dye to the vicinity of the stenosis is not needed.

The balloon catheter of the present invention as described can be utilized in the following manner to treat a stenosis as well as to prevent reoccurrence of the stenosis. Once the site of a stenosis is determined by appropriate diagnostic procedures, a small incision is made in the body and, assuming that an angioplasty procedure is necessitated, into a vessel. The guide wire 16 is then maneuvered into the vascular pathway and is imaged under fluoroscopy while being advanced through the blood vessel pass the area of stenosis. The catheter 12, with the balloon 18 being deflated, is threaded over the guide wire 16 and it is also advanced such that the balloon 18 is maneuvered to the area of the stenosis. Contrast dye is injected either through the external ports 28, 32 or the specially designed removable core guide wire illustrated in FIGS. 13, 14 and 15. The contrast dye enters the vascular pathway causing the blood vessel to become temporarily opaque and allowing it to be imaged under fluoroscopy.

Since the contrast media is quickly absorbed by the body, multiple injections of contrast dye are possible. An opaque marker can be applied to one or both ends of the ribbed balloon 18 allowing it to be imaged under fluoroscopy. Once the ribbed balloon is verified to be in position, the balloon is inflated, the guide wire is withdrawn from the body, and the angioplasty procedure commences.

At this point, the balloon 18 is inflated and deflated one or more times to widen the constricted area. When the balloon is deflated, contrast dye can be injected again to verify the widening of the prior constricted area. The balloon is then inflated to hold the catheter in place for the radioactive treatment.

One or more radioactive sources 38 are provided on, or inside the distal end of a flexible member 36 which is advanced through the interior of the catheter 12 until it reaches the proper location (see FIG. 4). The radioactive source treats the area of the original stenosis for a specific period of time. The time that the source remains inside the catheter depends upon the strength of the radioactive source and the distance between the source and the inner blood vessel walls. Examples of gamma type radiation sources which can be utilized in this procedure would be cesium 137, cobalt 60, iodine 125, iodine 131, cobalt 57, iridium 192, gold 198, palladium 103, etc. Typically, treatment times could last between approximately four minutes to approximately thirty minutes or longer. Since iridium 192 has a well-defined energy level with a strength of 1–2 Curies, it is particularly well-suited to treat the area of the original stenosis at the prescribed distance. In this instance, treatment times would be in the range of 5 to 10 minutes. After treatment with the radiation source has been completed, both the radiation source and the catheter, with the balloon deflated, are then removed from the body.

Since the radiation source can have a deleterious effect on the body if it is not precisely positioned with respect to the area of treatment, the present invention insures that the radiation source is positioned in the center of the vessel at a predetermined distance from the area of treatment. This is accomplished by inflating the ribbed balloon 18 when the radiation source is delivered to the proper location. Additionally, for safe measure, the balloon 18 can be inflated at all times when the radiation source is being delivered to the site of the treatment. The positioning of the radiation source with respect to the area of treatment is crucial since next to the radiation source, it is possible to receive thousands of Rads or centiGrays, units of measurement of radiation dose. This dosage would drop to only a few hundred Rads or centiGrays approximately 10 millimeters away from the source.

Although the present invention has been explained with respect to an angioplasty procedure, it is noted that this treatment could be conducted in virtually any conduit of the body with or without the inclusion of radiation treatment. This catheter can also be used to treat cancer in various areas of the body, such as the common bile duct, the bladder, the liver, the lungs, etc. employing the same balloon catheter shown in FIGS. 1–15.

There are many instances in the body where cancer invades around and into a vessel or airway. Treating and controlling the invasion of the cancer is difficult since a sealed prior art catheter having a removable backbone wire on its inside was used to try to access the cancerous area. Since the hollow duct of a vessel or other conduit includes many turns and bend inside the body, the cancerous area could not be reached due to the stiffness of the catheter and the fact that the backbone wire was unable to negotiate the turns. If the backbone wire was removed, the catheter would bunch up and advancement would not be possible. The balloon catheter of the present invention avoids these problems since a flexible guide wire is easily maneuvered into position and the closed-end catheter is advanced over this guide wire giving access to the cancerous area.

With this in mind, the following procedure can be utilized to treat a cancerous area with radiation utilizing the catheter, guide wire and sealing means illustrated in FIGS. 1–15: The radiopaque guide wire 16 is maneuvered into position either through a body orifice leading into the hollow duct or an opening created into the hollow duct by means of a small incision or puncture. The radiopaque nature of this guide wire allows X-rays to be used to properly position the guide wire beyond the tumor or cancerous site, which in many ways, is similar in appearance to the stenosis 30 of FIG. 1. The catheter system 10 is then threaded over the guide wire 16 and advanced into position. A radioptic marking on the ribbed balloon 18 makes it easy to position the catheter utilizing X-rays. To further confirm position of the catheter, a contrast dye may be injected through either of the external ports 28, 32 or through the removable guide wire illustrated in FIGS. 13–15. The balloon catheter is then inflated and the guide wire is removed. The inflation of the balloon is especially valuable if the tumor has invaded the duct or is causing extrinsic compression from outside the duct. This inflation will give temporary relief from the constriction, allowing greater passing of bodily fluids. A radioactive source or sources 38 contained on the end or inside the end of the flexible drive member 36 (FIG. 4) is advanced inside the catheter to align with the tumor or cancerous area. After a specified time, the radiation and catheter are removed from the body.

The catheter apparatus including the flexible membrane or the one-way valve is very important since, once the guide wire is removed, the system becomes closed, thereby not allowing the radioactive source or sources to advance out the end of a catheter and into the body if they become detached from the drive member 36. Furthermore, similar to the previously described embodiments, the inflated ribbed balloon allows body fluids to pass around the catheter. For example, when treating the bile duct, the catheter does not allow passage of the bile, cholecystitis can develop due to the back up of bile into the liver and cause liver dysfunction. Additionally, when treating the airway of the lung, if the catheter does not allow mucus or air to pass, atelectasis (collapsing of the lobe or the lung) or obstructive pneumonia can develop. This is a very harmful situation to the patient since the patient's lung capacity has already been compromised due to the presence of the cancer.

Similar to the previously described embodiments, the use of the inflated balloon catheter 18 is helpful in centering the radioactive source or sources inside the hollow duct. Since radiation emission observes the inverse square law, it is quite important that the radioactive source be properly centered because in areas of the body where the walls of the vessels are extremely radiosensitive, such as the bile duct, great harm can be caused to the patient if the source is not centered and kept from the vessel wall. Too much radiation for a period of time in an area proximate to the vessel wall can cause severe hemorrhaging or radiation necrosis.

Figure 16:
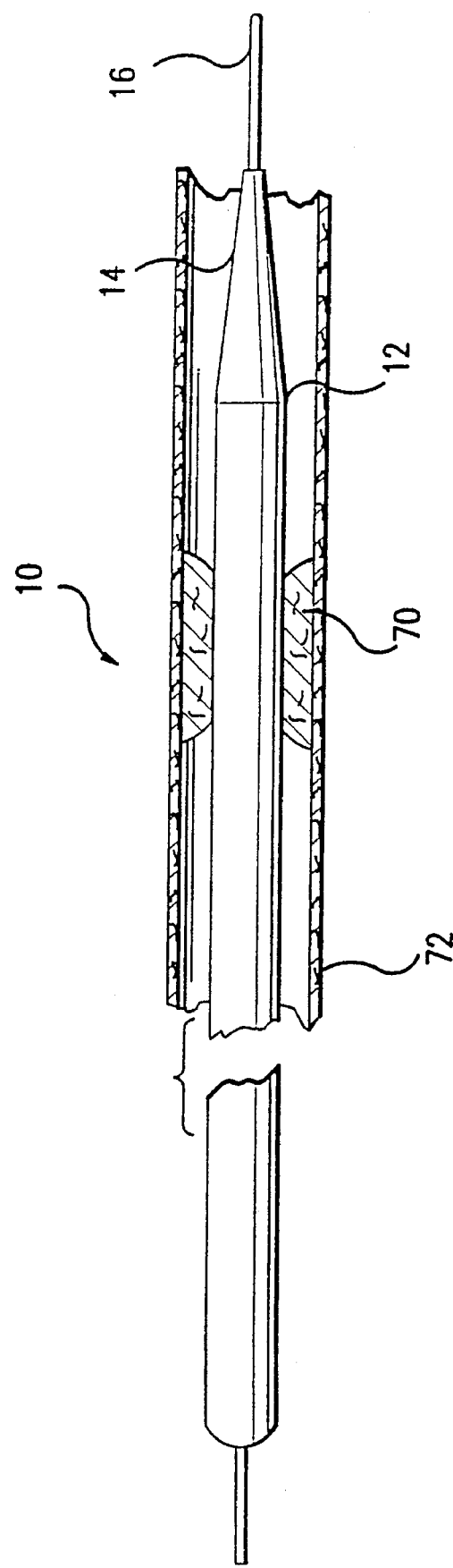
FIG. 16 is a side view of a catheter for the treatment of cancer within a vessel, duct or airway according to yet another embodiment of the present invention.

FIG. 16 illustrates a catheter and guide wire combination previously described, with the exception that a ribbed balloon or other means does not surround a portion of the exterior surface of the catheter. This catheter system is important since, in instances where a cancerous site 70 has invaded the vessel or duct wall 72 to a great extent, it would be very difficult if not impossible to maneuver a catheter having a ribbed balloon to the cancerous site. Once the guide wire 16 is removed, the radioactive source or sources is maneuvered in place in a manner similar to the above-described procedures relating to the treatment of stenosis or cancer.

Figure 17:
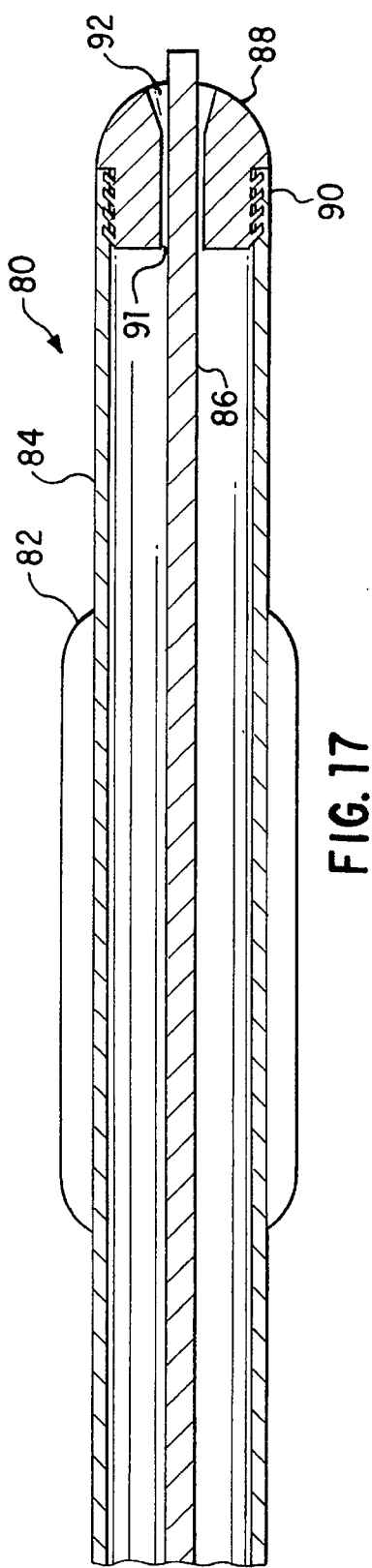
FIG. 17 is a longitudinal sectional view of another embodiment of the catheter according to the present invention.
Figure 18:
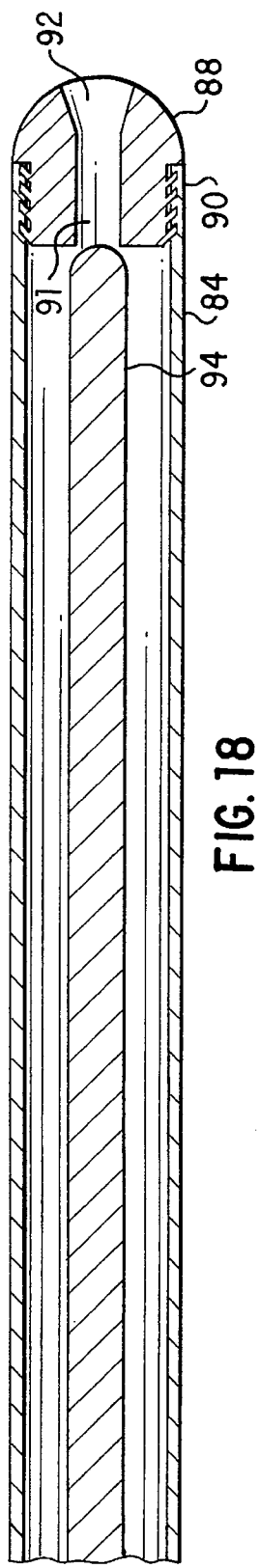
FIG. 18 is a longitudinal sectional view of the catheter shown in FIG. 17 including a radioactive source wire.

FIGS. 17–23 illustrate other embodiments of the present invention in which the radiation treatment source wire is prevented from being left behind in the body upon removal of the catheter therefrom. Even in situations in which the radioactive source wire breaks, the source wire will not remain inside the body. As shown in FIGS. 17 and 18, this is accomplished by utilizing a rounded constriction plug having the same outside or slightly larger diameter as the end of the catheter 84. The plug 88 is attached to the distal end of the catheter 84 by a multitude of techniques. For example, as shown in FIGS. 17–22, the constriction plug 88 can be crimped over the outside of the catheter 84 or locked in place with internal barbs on the inside of the catheter 84 as shown by 90. Additional methods of attachment, such as by pasting, gluing, welding, soldering, epoxying or the like can also be employed. It is important that the constriction plug be rounded to allow the catheter system to be advanced more easily and with less trauma within various bodily conduits as it is maneuvered into position. Without this rounded plug or end, the catheter's edge or end would nick the vessel wall as it is advanced, resulting in unnecessary trauma.

Since the catheter system 80 is advanced to the correct position in a manner similar to the technique described with respect to FIGS. 1–16, a guide wire 86 is first inserted into the catheter, with the catheter then being maneuvered to its correct location for treatment. Once the catheter system 80 is correctly positioned, the guide wire 86 is removed and a radioactive treatment source wire 94 is inserted and maneuvered through the catheter system until it is properly positioned. Therefore, to prevent the radioactive source wire 94 from exiting through the constriction plug 88, while allowing the guide wire 86 to move freely therein, the diameter of an internal passageway 91 of the plug 88 should be less than the diameter of the source wire 94, but greater than the diameter of the guide wire 86. The internal passageway 91 of the constriction plug is tapered at 92 to allow the guide wire to easily be inserted into and withdrawn from the constriction plug 88 and the catheter 84. Similar to the embodiment described with respect to FIGS. 1–16, the catheter system illustrated in FIG. 17 could also utilize an inflatable, ribbed balloon 82 to properly center the catheter when it has been maneuvered into its correct position.

Figure 19:
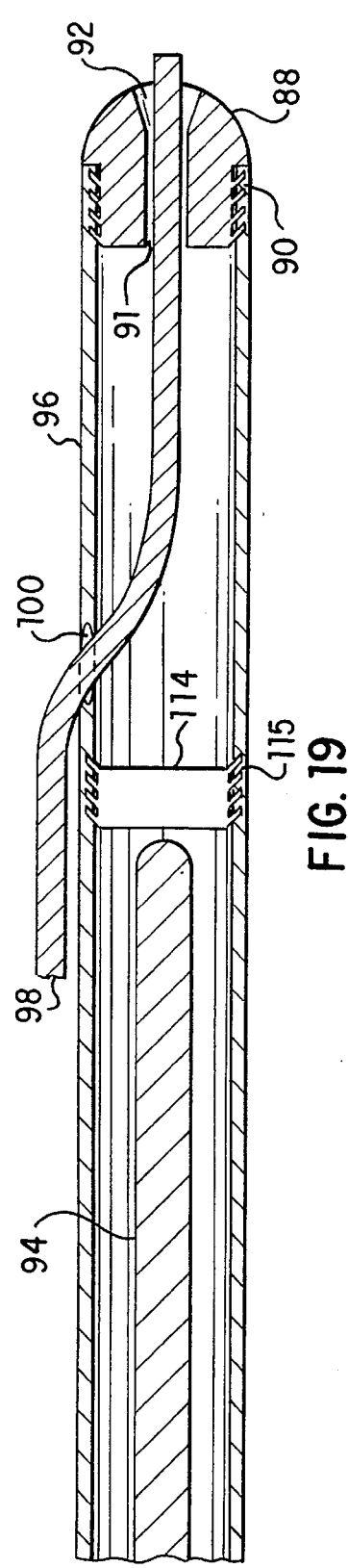
FIG. 19 is a longitudinal sectional view of another embodiment of the present invention utilizing a permanent plug.

FIGS. 17 and 18 illustrate an open channel catheter system 80 which would require that the radioactive source wire 94 be sterilized before insertion, or germs would enter the body. FIGS. 19, 20, 21 and 24 address this sterilization problem by utilizing a closed channel catheter system which would allow the advancement and placement of the treatment catheter without requiring that the radioactive source wire be sterilized. As shown in FIG. 19, a permanently affixed plug 114 is placed within a catheter 96, thereby blocking the movement of both the radioactive source wire 94 as well as a guide wire 98. Since the guide wire 98 cannot advance through the solid plug 114, the guide wire 98 remains outside of the catheter 96 for most of its length. A port 100 is provided on the side of the catheter 96 which would allow the guide wire 98 to enter the interior of the catheter between the position of the plug 114 and the constriction plug 88. This constriction plug 88 is similar in design to the plug which is used with respect to FIGS. 17 and 18. The plug 114 is affixed within the catheter 96 in a manner similar to that which was described with respect to affixing the constriction plug 88 to the end of the catheter with regard to FIGS. 17 and 18. Since the existence of the plug 114 would effectively prevent the radioactive source wire 94 from proceeding to the constriction plug 88, it is not crucial that the diameter of the internal passage 91 be greater than the diameter of the guide wire 98, but less than the diameter of the radioactive source wire 94. However, for ease of construction, it would be beneficial that the diameter of the internal passageway 91 be greater than the diameter of the guide wire 98, but less than the diameter of the radioactive source wire 94.

Figure 20:
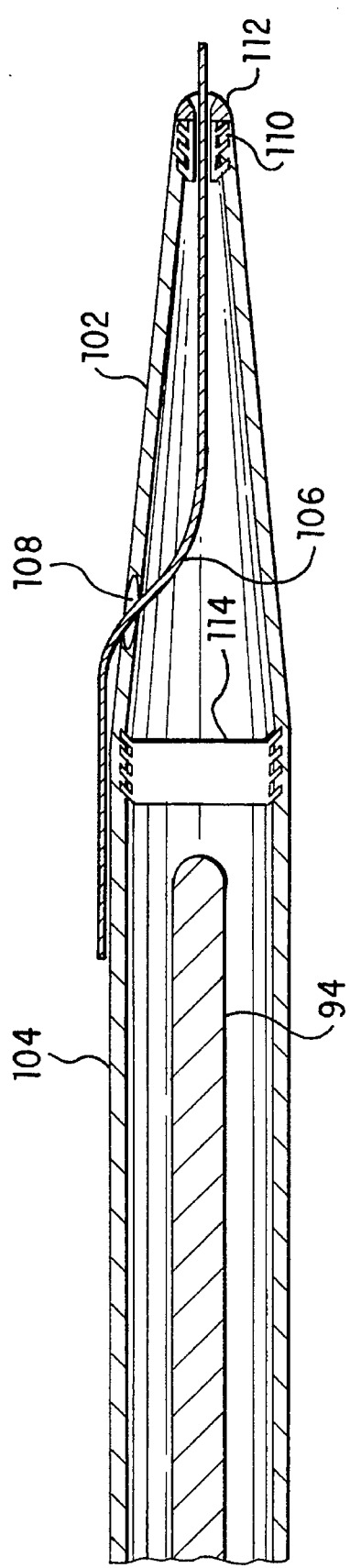
FIG. 20 is a longitudinal sectional view of the embodiment shown in FIG. 19 utilizing a tapered end.

FIG. 20 illustrates a catheter similar to the one which was described with respect to FIG. 19. However, the distal end 102 of this catheter is tapered and exhibits a smaller diameter than the main portion 104 of the catheter. This construction would allow for easier advancement into more restricted areas. In this situation, the guide wire 106 would be smaller in diameter than the guide wire 98 and would exit the interior of the catheter through a side port 108. The constriction plug 112 would be smaller than the size of the constriction plug 88. However, the plug 112 would be affixed to the catheter at 110 a the manner similar to that which has been described previously. It is also noted that guide wires 98, 106 would help anchor the catheter into position during treatment.

Figure 21:
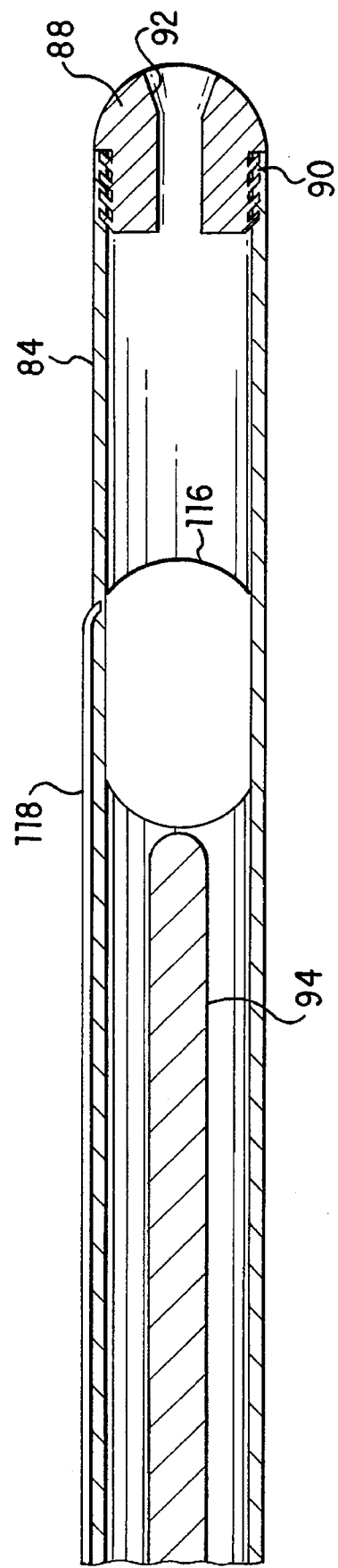
FIG. 21 is a longitudinal sectional view of another embodiment of the present invention utilizing an internal, inflatable sealing device.

FIG. 21 illustrates a closed catheter system which has already been maneuvered into place utilizing a guide wire. Once the guide wire has been used to properly position the catheter, it is removed and an internal balloon 116 is inflated utilizing inflation line 118, thereby completely sealing the inside of the catheter and providing the closed system. The balloon should not be deflated until the catheter exits the body, thereby insuring that no germs will enter the body. A constriction plug 88, similar to the plug described with respect to FIGS. 17–19 is attached to the distal end of the catheter.

Figure 22:
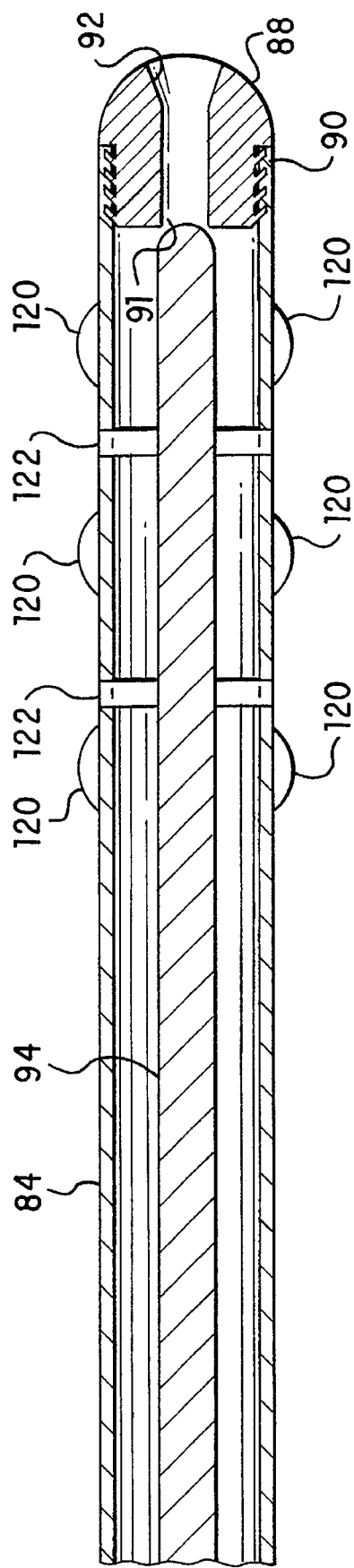
FIG. 22 is a longitudinal sectional view of another embodiment of the present invention provided with a non-inflatable centering device.
Figure 23:
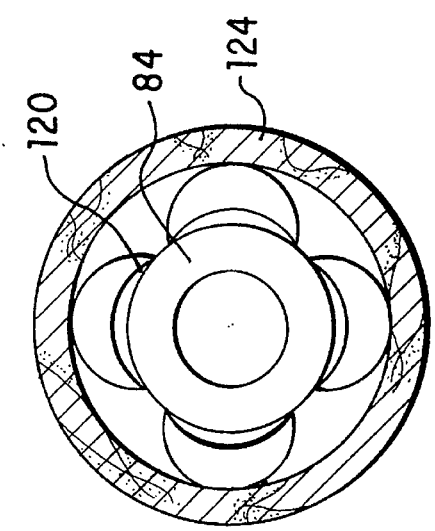
FIG. 23 is an end view of FIG. 22 with the catheter centered inside a bodily conduit.

FIGS. 22 and 23 illustrate an open catheter system after a guide wire has properly maneuvered the catheter into place. Similar to the description with respect to FIGS. 17 and 18, the diameter of the internal passageway 91 of the constriction plug 88 is less than the diameter of the radioactive source wire 94, but greater than the diameter of the guide wire. The catheter 84 is provided with radiopaque markings 122 in the vicinity of an external device on the catheter that centers the catheter inside the body. This external device takes the form of a plurality of strategically placed bumps or feelers 120 on the external surface of the catheter 84. These external devices are constructed from a very soft material, such as teflon, silicon, polyethylene glycol, etc. This material is not likely to induce trauma to a bodily conduit as the catheter is advanced into position. Since these bumps are placed on only several portions of the exterior of the catheter, it would allow bodily fluids to pass as illustrated in FIG. 23.

FIG. 24 illustrates a closed catheter system similar to FIG. 21. Once the guide wire has been used to properly position the catheter, it is removed and an internal balloon 116 is inflated utilizing inflation line 118, thereby completely sealing the inside of the catheter 84 allowing the balloon 116 to expand through these ports 132 to help center the catheter inside the bodily conduit. A hollow, flexible stent 130 is permanently attached to the balloon 116 to allow partial passage of the treatment wire 94. This hollow, flexible stent 130 is tapered at the entrance port 131 to allow easy passage of the treatment wire 94. This hollow, flexible stent 130 is hinged 133 at the opposite end inside the balloon 116. This hinge 133 allows the balloon 116 and stent 130 to lay flat when not inflated, so passage of a guide wire through the catheter 84 is possible. This hinged section 133 forms a closed end when the balloon 116 is inflated to prevent passage of the treatment wire 94. A constriction plug 88, similar to the plug described with respect to FIGS. 17–19, and 21 is attached to the distal end of the catheter.

FIG. 25 illustrates an end view of FIG. 24. The catheter 84 is centered inside the bodily conduit 124 by means of the balloon 116 exiting through the side portion openings 132 of catheter 84.

Figure 26:
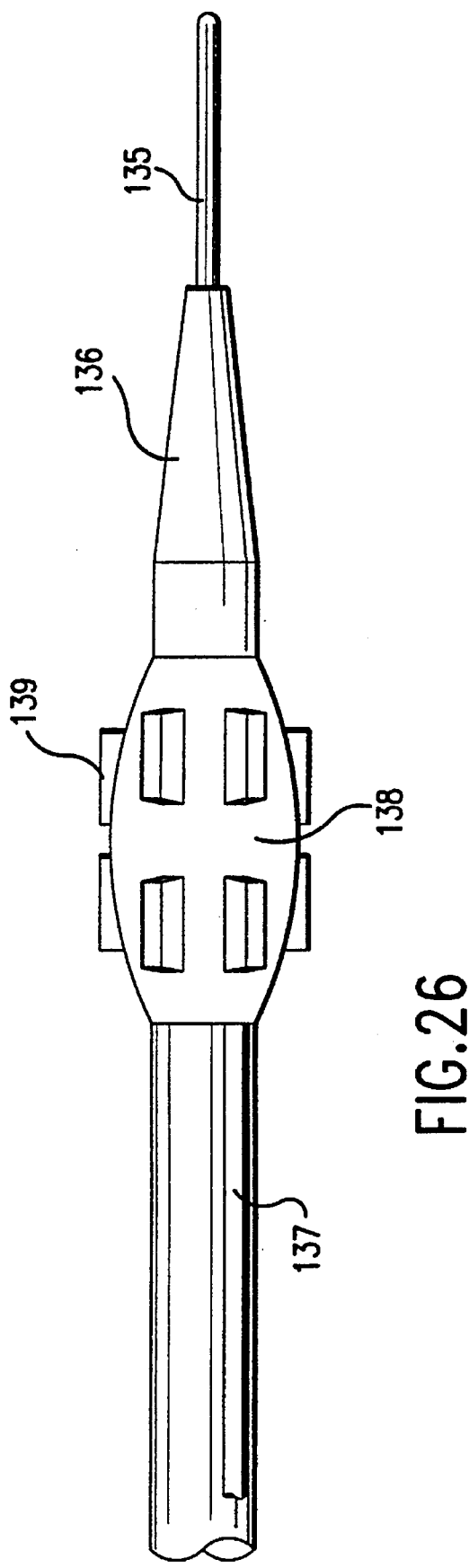
FIG. 26 is a side view showing raised devices permanently attached to a solid balloon.

FIG. 26 illustrates a closed catheter system similar to FIGS. 1, 2, 4 and 16 where the catheter is maneuvered into position by a guide wire 135. Instead of a balloon 18 that becomes ribbed when inflated as in FIGS. 1, 2, 4 and 16, a channel 137 is used to inflate a solid balloon 138 with permanently attached soft, flexible, raised portions 139. Upon inflation of the balloon 138, these soft, flexible raised portions 139 act as spacers between the balloon 138 and vessel wall, thus allowing the catheter 136 to be centered and at the same time allowing bodily fluids to pass.

Figure 27:
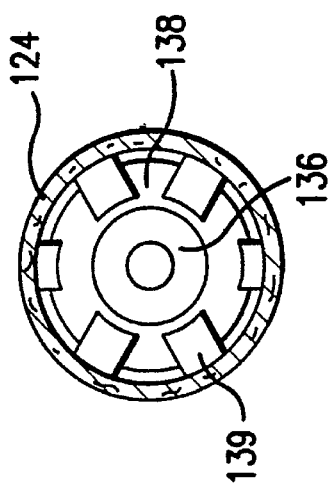
FIG. 27 is an end view of FIG. 26 with the catheter centered inside a bodily conduit.

FIG. 27 illustrates an end view of FIG. 26. The catheter 136 is centered within the bodily conduit 124. The raised portions 139 separates the balloon 138 from the vessel wall 124, thus allowing bodily fluids to pass.

Although preferred forms of the present invention have been herein disclosed, it is to be understood that the present disclosure is made by way of example and that variation of posture without departing from the scope of the hereinafter claimed subject matter. For example, both the constriction plug and the solid plug can be radiopaque.

What is claimed is:

1. A system for treating diseases in or around a narrow tortuous passageway in the body, comprising:

a flexible, elongated, catheter provided with a single hollow lumen having a distal end and a proximal end, said catheter provided with a first aperture;

a flexible, elongated guide wire having a first diameter through the narrow tortuous passageway, said guide wire inserted into at least a portion of said single hollow lumen of said catheter;

a radioactive elongated source wire having a second diameter, said radioactive elongated source wire inserted through said single hollow lumen of said catheter; and a constriction plug affixed to the termination of said distal end of said single hollow lumen of said catheter, said constriction plug including an interior passageway having a diameter which is greater than said first diameter, but less than said second diameter.

2. The system in accordance with claim 1, wherein the distal end of said constriction plug is rounded.

3. The system in accordance with claim 1, wherein said constriction plug is radiopaque.

4. The system in accordance with claim 1, further including a ribbed balloon provided with a plurality of lobes for centering said catheter provided with a single hollow lumen within a passageway in the body, and for opening an occlusion encircling a portion of said catheter proximate to said distal end, and a source for inflating said ribbed balloon.

5. The system in accordance with claim 1, further including a plurality of nodes provided on the exterior surface of said distal end of said catheter.

6. The system in accordance with claim 1, wherein a portion of said constriction plug extends beyond said termination of said distal end of said catheter.

7. The system in accordance with claim 1, wherein said constriction plug is provided with a plurality of barbs for attachment to said catheter.

8. The system in accordance with claim 1, wherein the diameter of said constriction plug is equal or slightly larger to the diameter of said catheter.

9. The system in accordance with claim 8, wherein the distal end of said constriction plug is rounded.

10. A system for treating diseases in or around a narrow tortuous passageway in the body, comprising:

a flexible, elongated, catheter provided with a single hollow lumen having a distal end and a proximal end, said catheter provided with a first aperture;

a flexible, elongated guide wire having a first diameter through the narrow tortuous passageway, said guide wire inserted into at least a portion of said single hollow lumen of said catheter;

a radioactive elongated source wire having a second diameter, said radioactive elongated source wire inserted through said single hollow lumen of said catheter; and a solid plug provided proximate to said distal end of said catheter for preventing both said guide wire and said source wire from passing therethrough, said solid plug provided within said single hollow lumen of said catheter.

11. The system in accordance with claim 10, further including a ribbed balloon provided with a plurality of lobes for centering said catheter within the passageway in the body, and for opening an occlusion encircling a portion of said catheter approximate to said distal end, and a source for inflating said ribbed balloon.

12. The system in accordance with claim 10, wherein said distal end has an exterior surface, and further including a plurality of nodes provided on said exterior surface of said distal end of said catheter.

13. The system in accordance with claim 10 further including a constriction plug affixed to said distal end of said catheter provided with said single hollow lumen, said constriction plug provided with an interior passageway; and an aperture provided through the surface of said catheter at a point between said solid plug and said constriction plug, wherein said guide wire is maneuvered through said aperture and said interior passageway of said constriction plug.

14. The system in accordance with claim 13, wherein said portion of said catheter between said solid and said constriction plug is tapered.

15. A system for treating diseases in or around a narrow tortuous passageway in the body, comprising:

a flexible, elongated, catheter provided with a single hollow lumen having a distal end and a proximal end, said catheter provided with a first aperture;

a flexible, elongated guide wire having a first diameter through the narrow passageway, said guide wire inserted into at least a portion of said single hollow lumen of said catheter;

a radioactive elongated source wire having a second diameter, said radioactive elongated source wire inserted through said single hollow lumen of said catheter; and a balloon provided proximate to said distal end of said catheter, said balloon provided within said catheter;

a conduit extending along the exterior surface of said catheter from said proximal end of said catheter to said balloon;

a source of inflation connected to said conduit for inflating said balloon to fill a portion of said hollow catheter to prevent both said guide wire and said source wire from passing therethrough; and a constriction plug affixed to the termination of said distal end of said single hollow lumen of said catheter, said constriction plug including an interior passageway having a diameter which is greater than said first diameter, but less than said second diameter.

16. A system for treating diseases in the body according to claim 15 wherein said balloon completely seals the interior of said catheter to prevent germs and bodily fluids from passing therethrough.

17. A system for treating diseases in or around a passageway in the body comprising:
- a flexible, elongated, catheter provided with a single hollow lumen having a distal end and a proximal end, said catheter provided with a plurality of openings between said proximal end and said distal end;
- a flexible, elongated guide wire having a first diameter through the narrow tortuous passageway, said guide wire inserted into at least a portion of of said single hollow lumen of the catheter;
- a radioactive elongated source wire having a second diameter, said radioactive elongated source wire inserted through said single hollow lumen of said catheter;
- a constriction plug affixed to said distal end of said single hollow lumen of said catheter, said constriction plug including an interior passageway having a diameter which is greater than said first diameter, but less than said second diameter;
- a balloon provided within said catheter when said balloon is in the deflated state, said balloon provided with a plurality of ribs which are provided adjacent to said plurality of openings;
- a conduit extending along the exterior surface of said catheter from said proximal end of said catheter to said balloon; and
- a source of inflation connected to said conduit for inflating said balloon, wherein when said balloon is inflated, said ribs of said balloon would be inflated through said opening of said catheter to center said catheter within the narrow, tortuous passageway in the body as well as to seal the interior of said catheter.

18. A system in accordance with claim 17 further including a hollow, flexible, stent provided within the interior of said balloon, said stent lying flat when said balloon is deflated.

19. A system in accordance with claim 18 wherein said stent is provided with a hinge forming a closed end when said balloon is inflated to prevent passage of said radioactive elongated source wire.

20. The system in accordance with claim 17, wherein said constriction plug is affixed to the termination of said distal end of said catheter.

21. The system in accordance with claim 20, wherein a portion of said constriction plug extends beyond said termination of said distal end of said catheter.

22. The system in accordance with claim 20, wherein said constriction plug is provided with a plurality of barbs, for attachment to said catheter.

* * * * *